United States Patent
Arai et al.

(10) Patent No.: US 8,598,292 B2
(45) Date of Patent: Dec. 3, 2013

(54) ADAMANTANE DERIVATIVE, METHOD FOR PRODUCING SAME, POLYMER USING SAME AS STARTING MATERIAL, AND RESIN COMPOSITION

(75) Inventors: Yoshihisa Arai, Tokyo (JP); Takehiko Isobe, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 67 days.

(21) Appl. No.: 13/254,231

(22) PCT Filed: Feb. 10, 2010

(86) PCT No.: PCT/JP2010/051971
§ 371 (c)(1),
(2), (4) Date: Sep. 1, 2011

(87) PCT Pub. No.: WO2010/101010
PCT Pub. Date: Sep. 10, 2010

(65) Prior Publication Data
US 2011/0319584 A1    Dec. 29, 2011

(30) Foreign Application Priority Data
Mar. 3, 2009    (JP) .................................. 2009-049224

(51) Int. Cl.
C08F 120/10        (2006.01)
C08L 33/04         (2006.01)
C07C 69/753        (2006.01)
G03F 7/039         (2006.01)
B05D 1/28          (2006.01)

(52) U.S. Cl.
USPC ............. 526/282; 526/75; 560/117; 560/220; 524/553; 430/270.1

(58) Field of Classification Search
USPC .......... 560/117, 220; 526/282, 75; 430/270.1; 524/553
See application file for complete search history.

(56) References Cited

U.S. PATENT DOCUMENTS

| | | |
|---|---|---|
| 5,665,518 A | 9/1997 | Maeda et al. |
| 6,391,520 B1 | 5/2002 | Nakano et al. |
| 6,656,659 B1 | 12/2003 | Nozaki et al. |
| 6,692,889 B1 * | 2/2004 | Funaki et al. .............. 430/270.1 |
| 7,078,562 B2 | 7/2006 | Furukawa et al. |
| 2003/0180662 A1 | 9/2003 | Nakano |
| 2004/0058270 A1 | 3/2004 | Iwai et al. |
| 2008/0063758 A1 | 3/2008 | Kwiat et al. |

FOREIGN PATENT DOCUMENTS

| | | |
|---|---|---|
| JP | H01-53633 B2 | 11/1989 |
| JP | H04-039665 A | 2/1992 |
| JP | H06-305044 A | 11/1994 |
| JP | H08-259626 A | 10/1996 |
| JP | H10-319595 A | 12/1998 |
| JP | 2000-122295 A1 | 4/2000 |
| JP | 2000-136165 A | 5/2000 |
| JP | 2003-167346 A | 6/2003 |
| JP | 2006-016379 A | 1/2006 |

OTHER PUBLICATIONS

Kikuo Furukawa et al., "Evaluation of adamantane derivatives for chemically amplified resist—a comparison between ArF, EUV and EB exposures", Proc. of SPIE, vol. 6923-123, (2008) 11 pages.
International Search Report issued in International Application PCT/JP2010/051971, dated Apr. 20, 2010.

* cited by examiner

*Primary Examiner* — Fred M Teskin
(74) *Attorney, Agent, or Firm* — Fitch, Even, Tabin & Flannery LLP (57) ABSTRACT

Provided are an adamantane derivative represented by the following formula (1), a method for producing the same, a polymer containing an acrylate compound having the adamantane structure represented by formula (1) in a repeat unit, and a functional resin composition which contains the polymer, has excellent alkali developability and substrate adhesiveness, and can improve the resolution and the line edge roughness as a chemically amplified resist sensitive to far-ultraviolet rays represented by KrF excimer laser light, ArF excimer laser light, $F_2$ excimer laser light or EUV without spoiling fundamental properties thereof as a resist such as pattern forming properties, dry etching resistance, heat resistance and the like.

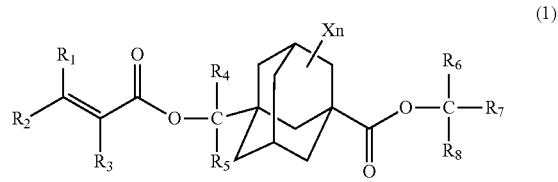

(1)

In the formula, $R_1$ through $R_3$, which may be the same or different, each represent a hydrogen atom, an alkyl group having a carbon number of 1 to 3, or a halogen-containing alkyl group; $R_4$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or a alkoxy group having a carbon number of 1 to 3; and n represents 14.

6 Claims, 4 Drawing Sheets

FIG. 1

¹H-NMR (deuterated chloroform):
3-(1-hydroxy-1-methylethyl)adamantane-1-carboxylic acid t-butyl ester

FIG. 2

¹H-NMR (deuterated chloroform):
3-(1-methacryloyloxy-1-methylethyl)adamantane-1-carboxylic acid t-butyl ester

FIG. 3

X: parts per Million :13C $^{13}$C-NMR (deuterated chloroform):
3-(1-methacryloyloxy-1-methylethyl)adamantane-1-carboxylic acid t-butyl ester

FIG. 4

IR (KBr method):
3-(1- methacryloyloxy-1-methylethyl)adamantane-1-carboxylic acid t-butyl ester

ADAMANTANE DERIVATIVE, METHOD FOR PRODUCING SAME, POLYMER USING SAME AS STARTING MATERIAL, AND RESIN COMPOSITION

CROSS-REFERENCE TO RELATED APPLICATIONS

This is a U.S. National Phase of International Application PCT/JP2010/051971, filed Feb. 10, 2010, and claims the benefit of foreign priority from Japanese Patent Application 2009-049224, filed Mar. 3, 2009, the entire disclosures of which applications are hereby incorporated herein by reference.

TECHNICAL FIELD

The present invention relates to a functional resin composition which has high optical characteristics, high heat resistance, high optical transparency and the like, and is usable for optical materials such as crosslinked resins, optical fibers, optical waveguides, optical disc substrates, resists for KrF, ArF and $F_2$ excimer lasers and chemically amplified resists for X rays, electron beams and EUV (extreme ultraviolet light), usable for materials of the optical materials, usable for pharmaceutical and agricultural intermediates, and usable for various other industrial products; a polymer usable for the composition; an adamantane derivative (acrylate compound having an adamantane skeleton), which is a material of the polymer; and a method for producing the adamantane derivative.

BACKGROUND ART

Adamantane has a rigid structure and is highly symmetrical, and a derivative thereof exhibits a specific function. For these reasons, adamantane is known to be useful for highly functional resin materials, pharmaceutical intermediates, and optical materials (see Patent Documents 1 and 2), especially for photoresists (see Patent Document 3).

A resin composition for a photoresist, which is used in a semiconductor production process, needs to have characteristics, such as a property of becoming alkali-soluble when irradiated with light, etching resistance, substrate adhesiveness, transparency to a light source to be used, and the like, in a good balance. When the light source to be used is a KrF excimer laser or any other short-wavelength light source developed after the KrF excimer laser, a chemically amplified resist is generally used. The composition of such a chemically amplified resist is generally used in the form of a solution containing a resin composition as a main component, a photoacid generator and several types of additives. It is important that, among these components, the resin composition as the main component has the above-mentioned characteristics in a good balance, and the balance of the characteristics determines the performance of the resist.

When the light source to be used is a KrF excimer laser or any other short-wavelength light source developed after the KrF excimer laser, a chemically amplified resist is used. The resin composition of the chemically amplified resist, which is the main component, is generally a polymer containing acrylate or the like as a repeat unit. However, the acrylate or the like is not used as a single repeat unit. A reason for this is that a single repeat unit cannot fulfill the requirements for all the characteristics including the etching resistance. In actuality, a plurality of repeat units each having a functional group for improving each of the characteristics are used. Namely, the resin composition used is formed of a copolymer of two or more types of polymers. For a resist to be used in KrF excimer laser lithography, a hydroxystyrene-based resin is proposed; and for a resist to be used in ArF excimer laser lithography, an acrylic-based resin having 2-alkyl-2-adamantyl methacrylate as a skeleton is proposed (see Patent Documents 3 and 4).

However, recently, lithography processes have been developed so as to be usable for more and more reduced sizes, and are now required to allow each type of light source to be usable for a line width which is at most about ⅓ of the corresponding wavelength. Especially, ArF excimer laser lithography is required to be usable for a still thinner line width by means of application of immersion technology or introduction of double patterning technology. As the line width has become thinner, demands for the sensitivity, resolution, line edge roughness and the like have become more strict.

For solving these problems, it has been studied to copolymerize an existing resin with any of various acrylate compounds or to significantly change the structure itself of the existing resin. For example, a resist composition has been proposed which contains an adamantane derivative having features that the surface is not much roughened by etching, the line edge roughness is small, and the like (see Patent Document 5). However, it is currently difficult to fulfill the requirements, imposed by the reduction in the line width, for the resolution, line edge roughness and the like.

CITATION LIST

Patent Document

Patent Document 1: Japanese Laid-Open Patent Publication No. H6-0305044
Patent Document 2: Japanese Patent Publication for Opposition No. H1-53633
Patent Document 3: Japanese Laid-Open Patent Publication No. H4-39665
Patent Document 4: Japanese Laid-Open Patent Publication No. H10-319595
Patent Document 5: Japanese Laid-Open Patent Publication No. 2003-167346
Patent Document 6: Japanese Laid-Open Patent Publication No. 2000-122295
Patent Document 7: Japanese Laid-Open Patent Publication No. 2006-016379
Patent Document 8: Japanese Laid-Open Patent Publication No. 2000-136165

Non-Patent Document

Non-patent Document 1: SPIE, 6923-123 (2008)

SUMMARY OF INVENTION

Problem to be Solved by Invention

Under these circumstances, an excellent functional resin composition is strongly desired to be developed, which can improve the sensitivity, resolution and line edge roughness without exerting any adverse effect on the fundamental characteristics of the resin composition. In the course of the studies, it has been shown that an alcoholic hydroxyl group contained in a resin composition tends to improve the sensitivity or resolution (see Non-patent Document 1). As an example of resin containing a monomer having an alcoholic hydroxyl group, a resin containing 3,5-dihydroxy-1-adamantyl (meth)

acrylate which contains two alcoholic hydroxyl groups, has been proposed (see Patent Document 6). This resin is expected to provide high resist performances such as high sensitivity and high resolution. A resist monomer contained in a resist polymer and having acid dissociation characteristics usually does not contain an alcohol hydroxyl group. However, among such resist monomers, as a resist monomer containing one alcoholic hydroxyl group and also having acid dissociation characteristics, 3-(1-hydroxy-1-methylethyl)-1-(1-methacryloyloxy-1-methylethyl)adamantane has been proposed (Patent Document 7) and is expected to provide high resist performances such as high sensitivity and high resolution. Patent Document 8 describes acid-sensitive compounds containing a monocyclic or polycyclic aliphatic ring having an alcoholic hydroxyl group as a substituent (see Examples) and discloses that such compounds are useful as compositions for photoresists.

Means for Solving Problem

An object of the present invention is to provide an adamantane derivative having an adamantane skeleton and useful as, for example, a crosslinked resin having high optical characteristics and the like and a monomer usable therefor, and a method for producing the same.

Another object of the present invention is to provide a functional resin composition which has high alkali developability and high substrate adhesiveness, and can improve the resolution and line edge roughness as a chemically amplified resist sensitive to far-ultraviolet rays represented by KrF excimer laser light, ArF excimer laser light, $F_2$ excimer laser light or EUV without spoiling fundamental properties thereof as a resist such as pattern forming properties, dry etching resistance, heat resistance and the like; and a material compound (polymer) thereof. A functional resin compound according to the present invention is preferable as a resin compound for a resist.

The present inventors, as a result of active studies on the above-described problems, found that an acrylate compound derived from an adamantane structure represented by formula (1) contains an acid-dissociable tertiary ester group in an acid-dissociable adamantane skeleton and so is expected to have the acid-dissociable group removed easily at the time of alkali development, and that this compound is suitable for the above objectives. The present inventors also found that a polymer which has, as a material, an acrylate compound having an adamantane structure represented by formula (1) and contains a repeat unit represented by formula (2), and a functional resin composition containing such a polymer, are expected to be useful for a photoresist; and arrived at the present invention.

[Chemical formula 1]

(1)

(in the formula, $R_1$ through $R_3$, which may be the same or different, each represent a hydrogen atom, an alkyl group having a carbon number of 1 to 3, or a halogen-containing alkyl group; $R_4$ through $R_9$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 14.)

[Chemical formula 2]

(2)

(in the formula, $R_1$ through $R_3$, which may be the same or different, each represent a hydrogen atom, an alkyl group having a carbon number of 1 to 3, or a halogen-containing alkyl group; $R_4$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 14.)

Still another object of the present invention is to provide a method for producing an adamantane derivative represented by formula (1) by reacting an adamantane alcohol represented by the following formula (8) with an acrylic acid compound represented by the following formula (9) or (10).

[Chemical formula 3]

(8)

(in the formula, $R_4$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 14.)

[Chemical formula 4]

(9)

(in the formula, $R_1$ through $R_3$, which may be the same or different, each represent a hydrogen atom, an alkyl group having a carbon number of 1 to 3, or a halogen-containing alkyl group; and Z represents a hydroxyl group, an alkoxy group, or a halogen group.)

[Chemical formula 5]

(10)

(in the formula, $R_1$ through $R_3$, which may be the same or different, each represent a hydrogen atom, an alkyl group having a carbon number of 1 to 3, a halogen-containing alkyl group, or a halogen group.)

Advantageous Effects of Invention

An adamantane derivative according to the present invention is useful for optical materials such as crosslinked resins, optical fibers, optical waveguides, optical disc substrates, photoresists and the like, for materials of the optical materials, for pharmaceutical and agricultural intermediates, and for various other industrial products. A polymer and a functional resin composition according to the present invention are usable for materials of resists for KrF, ArF and $F_2$ excimer lasers and chemically amplified resists for X rays, electron beams and EUV (extreme ultraviolet light). Such a resin composition for resists is expected to have high etching resistance, exhibits high adhesiveness to substrates, have alkali-solubility, and to be capable of forming a pattern of high sensitivity and high resolution at high precision.

EMBODIMENTS OF INVENTION

First, an acrylate compound having an adamantane structure according to the present invention, and a polymer and a functional resin composition each having the acrylate compound as a material, will be described.
An adamantane derivative represented by formula (1) is obtained from an adamantane represented by formula (3) as a starting material. Compounds represented by formula (3) include 1,3-adamantanediol, 3-bromo-1-adamantanol, 1,3-dibromoadamantane, and the like.

[Chemical formula 6]

(3)

(in the formula, X, which may be the same or different, represents a hydrogen atom, an alkyl group having a carbon number of 1 to 3, or an alkoxy group having a carbon number of 1 to 3; $Y_1$ and $Y_2$ represent a hydroxyl group or a halogen group; and n represents 14.)

The adamantane represented by formula (3) is subjected to a carboxylation reaction with carbon monoxide or carbon monoxide source in the presence of a protonic acid. As a result, an adamantanedicarboxylic acid represented by formula (4) can be synthesized at high selectivity and high yield.

[Chemical formula 7]

(4)

Usable protonic acids include organic acids (organic carboxylic acids such as formic acid, acetic acid, propionic acid, oxalic acid, citric acid, tartaric acid and the like; organic sulfonic acids such as methanesulfonic acid, benzenesulfonic acid, p-toluenesulfonic acid and the like; etc.) and inorganic acids (e.g., hydrochloric acid, sulfuric acid, nitric acid, phosphoric acid, and the like). Among these, concentrated sulfuric acid, which is low-cost and easy to handle, is desirable for use.
The concentrated sulfuric acid is used in the form of an aqueous solution having a concentration of preferably, 90% by weight or higher, and more preferably, 96% by weight or higher. When the concentration is lower than the above range, the substituents ($Y_1$, $Y_2$) are not sufficiently converted into carboxylic acid groups.
The amount of the concentrated sulfuric acid to be used is 2 to 20 times by weight, preferably 4 to 16 times by weight, and more preferably 8 to 12 times by weight, with respect to the adamantane represented by formula (3). When the amount is larger than the above range, the substituents ($Y_1$, $Y_2$) are not sufficiently converted into carboxylic acid groups. Even when the amount is larger than the above range, the yield does not rise.
Carbon monoxide used in the carboxylation reaction may be pure carbon monoxide or diluted with inert gas. Carbon monoxide may be used under normal pressure or in a state pressurized by an autoclave.
The amount of the carbon monoxide may be selected from the range of 1 equivalent with respect to the substrate (in this case, when two carboxylic groups are introduced, 2 mots of carbon monoxide are present with respect to 1 mol of substrate) to 1000 equivalents with respect to the substrate. The amount is preferably about 1 to 10 equivalents, and more preferably about 1 to 3 equivalents with respect to the substrate. When the amount is smaller than the above range, the yield falls, needless to say, and even when the amount is larger than the above range, the yield does not rise. Instead of carbon monoxide, formic acid or formic alkyl may be used as the carbon monoxide source. Even in such a case, the amount is the same. When the amount is smaller than the above range, the yield falls, needless to say, and even when the amount is larger than above range, the yield does not rise.

For the carboxyl group introduction reaction, protonic acid may be used as a solvent. An inactive organic solvent may be used. Usable organic solvents include, for example, organic carboxylic acids such as acetic acid and the like; nitriles such as acetonitrile, benzonitrile and the like; amides such as formamide, acetamide, dimethylformamide, dimethylacetamide and the like; aliphatic hydrocarbons such as hexane, octane and the like; halogenated hydrocarbons; nitro compounds; ethers such as tetrahydrofuran, diethylether, diisopropylether, dioxane and the like; and mixed solvents thereof.

The carboxylation reaction smoothly proceeds even under relatively mild conditions. The reaction temperature is, for example, about −78 to 200° C., and preferably about −20 to 100° C. Usually, the reaction often occurs at about 0 to 80° C. When the temperature is lower than the above range, the reaction does not sufficiently proceed. When the temperature is higher than the above range, a side reaction proceeds to lower the yield. The reaction can be carried out at normal pressure or under a pressurized state.

The reaction time is usually 1 to 100 hours, and preferably 1 to 10 hours. When the reaction time is shorter than the above range, the carboxylation reaction does not sufficiently proceed. Even when the reaction time is longer than the above range, the yield does not rise.

After the reaction is completed, the reaction solution is mixed with water or an alkaline aqueous solution. As a result, the adamantanedicarboxylic acid represented by formula (4) is deposited and thus can be obtained. After being mixed with the alkaline aqueous solution, the reaction solution needs to be made acidic again.

Among the methods described above, the method of using 1,3-adamantanediol as the adamantane, using concentrated sulfuric acid as the protonic acid, and using formic acid as the carbon monoxide source is preferable because this method is simple, can be carried out with a mild liquid phase reaction, and provides the adamantanedicarboxylic acid represented by formula (4) with high selectivity and high yield.

Next, the adamantanedicarboxylic acid represented by formula (4) is alkylesterified to synthesize an adamantanedicarboxylic acid ester represented by formula (5).

[Chemical formula 8]

(5)

(in the formula, X, which may be the same or different, represents a hydrogen atom, an alkyl group having a carbon number of 1 to 3, or an alkoxy group having a carbon number of 1 to 3; $R_9$ and $R_{10}$ each represent an alkyl group having a carbon number of 1 to 6; and n represents 14.)

The alkylesterification may be performed by once taking out the adamantanedicarboxylic acid represented by formula (4) and then reacting the same with corresponding alcohol under the presence of a protonic acid catalyst, or by first reacting the adamantane represented by formula (3) with protonic acid/carbon monoxide or carbon monoxide source and then adding corresponding alcohol to the resulting substance to cause a reaction. Usable alcohols include methanol, ethanol, propanol, butanol, pentanol, hexanol, and cyclohexanol. The reaction temperature is 0 to 150° C., and the reaction time before the completion of the reaction is 1 to 5 hours. After the reaction is completed, the resultant substance is subjected to extraction into an organic solvent and then washing with water or an alkali such as an aqueous solution of sodium hydroxide. Then, the adamantanedicarboxylic acid ester represented by formula (5) can be obtained a known technique such as concentration, recrystallization, column chromatography or the like.

Organic solvents usable for the reaction or the extraction include aromatic compounds such as benzene, toluene, xylene, mesitylene, cumene, ethylbenzene, pseudocumene and the like; esters such as methyl acetate, ethyl acetate, propyl acetate, butyl acetate, pentyl acetate, hexyl acetate, methyl formate, ethyl formate, propyl formate, butyl formate, pentyl formate, hexyl formate, methyl propionate, ethyl propionate, propyl propionate, butyl propionate, pentyl propionate, hexyl propionate and the like; alcoholic compounds such as butanol, pentanol, hexanol, heptanol, octanol and the like; and ether compounds such as tetrahydrofuran, diethylether, diisopropylether, methyl-t-butylether, dioxane and the like.

Next, the adamantanedicarboxylic acid ester represented by formula (5) is reacted with an organic metal compound to synthesize an adamantanemonocarboxylic acid ester represented by formula (6).

[Chemical formula 9]

(6)

(in the formula, $R_4$ and $R_5$, which may be the same or different, each represent an alkyl group having a carbon number of 1 to 3 or a halogen-containing alkyl group; $R_9$ represents an alkyl group having a carbon number of 1 to 6; X, which may be the same or different, represents a hydrogen atom, an alkyl group having a carbon number of 1 to 3, or an alkoxy group having a carbon number of 1 to 3; and n represents 14.)

Usable organic metal compounds are corresponding alkyl lithium and halogenated alkyl magnesium. Instead of such an organic metal compound, a mixture of halogenated alkyl and lithium metal or a mixture of halogenated alkyl and magnesium metal may be directly reacted by a Barbier reaction (hereinafter, these compounds will be collectively referred to as the "organic metal compounds"). The amount of the organic metal compound is desirably 0.5 to 1 equivalent (1 equivalent is 3 times by mol with respect to 1 mol of the material). When the amount is smaller than the above range, the reaction does not sufficiently proceed. When the amount is larger than the above range, the reaction proceeds excessively and dialcohol is formed, and so the yield falls. As the solvent, anything inactive to the reaction is usable with no specific limitation. Usable solvents include ethers such as tetrahydrofuran, dithylether, diisopropylether, methyl-t-butylether, dioxane and the like; aliphatic hydrocarbons such as hexane, heptane, octane, nonane, decane, cyclohexane and the like; and aromatic compounds such as benzene, toluene, xylene, trialkylbenzene, ethylbenzene, cumene and the like.

There is no specific limitation on the method for mixing the organic metal compound and the adamantanedicarboxylic acid ester represented by formula (5). The organic metal compound may be dissolved in a solvent, and the material dissolved in a solvent may be dropped thereto. Alternatively, oppositely, the material may be dissolved in a solvent, and the organic metal compound diluted with a solvent may be dropped thereto. It should be noted that heat is generated at the tine of mixing and so it is preferable to avoid an abnormal temperature rise. The temperature at the time of mixing is desirably 0 to 100° C.

After the mixing, it is preferable to cause the reaction at the temperature of 0 to 100° C. After the reaction is completed, the reaction is stopped with water or alcohol, and the adamantanemonocarboxylic acid ester represented by formula (6) can be obtained by a known technique such as extraction, concentration, recrystallization, column chromatography or the like.

Next, the adamantanemonocarboxylic acid ester represented by formula (6) is subjected to a transesterification reaction with an alcohol represented by formula (7) to synthesize an adamantane alcohol represented by formula (8).

The alcohol represented by formula (7) is used in an amount 0.5 to 100 times, and preferably 3 to 20 times, by mol with respect to the adamantanemonocarboxylic acid ester represented by formula (6). Usable reaction solvents include ethers such as tetrahydrofuran, diethylether, diisopropylether, methyl-t-butylether, dioxane and the like; aliphatic hydrocarbons such as hexane, heptane, octane, nonane, decane, cyclohexane and the like; and aromatic compounds such as benzene, toluene, xylem, trialkylbenzene, ethylbenzene, cumene and the like.

The reaction is usually carried out under alkaline conditions or neutral conditions. When the reaction is carried out under alkaline conditions, an alkali metal, a hydride thereof alkoxide or the like can be added. When the reaction is carried out under neutral conditions, titanium alkoxide or the like can be added. The reaction temperature is, for example, about 20 to 200° C., and preferably about 5 to 150° C. In order to promote the reaction, the reaction can be carried out while the produced alcohol is removed.

Next, the adamantane alcohol represented by formula (8) is subjected to an esterification reaction with (meth)acrylic acid or a derivative thereof (hereinafter, referred to as the "acrylic acid compound"). As a result, the target compound is obtained.

The adamantane alcohol represented by formula (8) may be used as it is, or may be used with a hydroxyl group being replaced with an alkali metal such as lithium, sodium or the like, or halogenated magnesium. The esterification reaction with an acrylic acid compound represented by formula (9) or (10) can be caned out by a common technique using an acid catalyst, a base catalyst or a transesterification catalyst.

[Chemical formula 10]

(7)

(in the formula, $R_6$ through $R_8$, which may be the same or different, each represent an alkyl group having a carbon number of 1 to 3 or a halogen-containing alkyl group; and M represents a hydrogen atom or an alkali metal.)

[Chemical formula 11]

(8)

(in the formula, $R_4$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 1-4.)

[Chemical formula 12]

(9)

($R_1$ through $R_3$, which may be the same or different, each represent a hydrogen atom, an alkyl group having a carbon number of 1 to 3, or a halogen-containing alkyl group; and Z represents a hydroxyl group, an alkoxy group or a halogen group.)

[Chemical formula 13]

(10)

(in the formula, $R_1$ through $R_3$, which may be the same or different, each represent a hydrogen atom, an alkyl group having a carbon number of 1 to 3, a halogen group, or a halogen-containing alkyl group.)

Specific examples of the acrylic acid compound include acid compounds such as acrylic acid, methacrylic acid, 2-fluoroacrylic acid, trifluoroacrylic acid, 2-(trifluoromethyl) acrylic acid and the like; acrylic acid halides such as acrylic acid chloride, methacrylic acid chloride, 2-fluoroacrylic acid chloride, trifluoroacrylic acid chloride, 2-(trifluoromethyl) acrylic acid chloride and the like; acrylic acid esters such as methyl acrylate, ethyl acrylate, t-butyl acrylate, methyl methacrylate, ethyl methacrylate, t-butyl methacrylate, methyl trifluoroacrylate, ethyl trifluoroacrylate, isopropyl trifluoroacrylate, trifluoroacrylic acid-t-butyl, methyl pentafluoromethacrylate, ethyl pentafluoromethacrylate, isopropyl pentafluoromethacrylate, pentafluoromethacrylic acid-t-butyl, methyl 2-fluoroacrylate, ethyl 2-fluoroacrylate, isopropyl 2-fluoroacrylate, 2-fluoroacrylic acid-t-butyl, methyl 2-(trifluoromethyl)acrylate, ethyl 2-(trifluoromethyl) acrylate, isopropyl 2-(trifluoromethyl)acrylate, 2-(trifluoromethyl)acrylic acid-t-butyl and the like; acrylates such as sodium acrylate, sodium methacrylate, sodium 2-fluoroacrylate, sodium trifluoroacrylate, sodium 2-(trifluoromethyl) acrylate and the like; and acrylic acid anhydrides such as acrylic anhydride, methacrylic anhydride, perfluoroacrylic anhydride, perfluoromethacrylic anhydride, 2,2'-difluoroacrylic anhydride, 2-fluoroacrylic anhydride, 2-trifluoromethylacrylic anhydride and the like. The amount to be used is 1 to 100 equivalents, and preferably 1 to 10 equivalents, with respect to the material. When the amount is smaller than the above range, the yield falls. When the amount is larger than the above range, it is not economical.

In order to react the adamantane alcohol represented by formula (8) with an acrylic acid compound rapidly at high yield, it is preferable that an additive is present. When an acid halide or an acrylic anhydride is used as the acrylic acid compound, it is desirable that a basic compound is present as an additive. Namely, when an acid halide compound or an acrylic anhydride represented by acrylic acid chloride, methacrylic acid chloride, acrylic anhydride, methacrylic anhydride or the like is used as an acrylic acid compound, coexistence of a basic compound allows the reaction to proceed rapidly. As a result, the target substance is obtained at high yield. As the basic compound, any organic base is usable. Examples of the organic base include amines such as methylamine, dimethylamine, trimethylamine, ethylamine, diethylamine, triethylamine, n-propylamine, di-n-propylamine, diisopropylamine, tri-n-propylamine, n-butylamine, di-n-butylamine, diisobutylamine, tri-n-butylamine, diphenylamine, 1,5-diazabicyclo[4.3.0]nonene-5,1,5-diazabicyclo[5.4.0]undecene-5, diazabicyclo[2.2.2]octane and the like; anilines, which are also organic amines, such as aniline, methylaniline, dimethylaniline, toluidine, anisidine, chloroaniline, bromoaniline, nitroaniline, aminobenzoic acid and the like; and nitrogen-containing heterocyclic compounds such as pyridines, e.g., pyridine, dimethylaminopyridine, etc. pyrroles, quinolines, piperidines and the like. The reaction solution may contain any of the following: metal alkoxides such as sodium methoxide, lithium methoxide and the like; quaternary ammonium hydroxides such as tetramethylammonium hydroxide, trimethyl-n-propylammonium hydroxide and the like; sulfates, nitrates, chlorides, etc. of amine such as ethylammonium sulfate, trimethylammonium nitrate, anilinium chloride and the like; inorganic bases such as sodium hydrogencarbonate and the like; and Grignard reagents such as ethylmagnesium bromide and the like.

The amount of such an additive is preferably 10 equivalents or less with respect to the material. No effect of adding such an additive is provided when the amount is larger than the above range. There is no specific limitation on the method for adding a basic compound. A basic compound may be added before the acrylic acid compound is added, or after the acrylic acid compound is added. A basic compound may be dropped at the same time as the acrylic acid compound. In this case, it is desirable to control the reaction temperature not to rise abnormally because by such a control, a side effect is suppressed from proceeding. As a solvent, a substance in which the material and the target substance are highly soluble is desirable. Such solvents include halogen compounds such as dichloromethane, chloroform, 1,2-dichloroethane and the like; ether compounds such as tetrahydrofuran, dioxane, diethylether, propylether, methyl-t-butylether and the like; aliphatic hydrocarbons having a carbon number of 6 to 10 such as hexane, heptane, octane, nonane, decane and the like; alicyclic hydrocarbons having a carbon number of 6 to 10 such as cyclohexane, methylcyclohexane, dimethylcyclohexane, ethylcyclohexane and the like; and aromatic hydrocarbons such as benzene, toluene, xylene, trialkylbenzene, ethylbenzene, cumene and the like. The reaction temperature is −70 to 200° C. and preferably −50 to 80° C. When the reaction temperature is lower than −70° C., the reaction rate is lowered; and when the reaction temperature is higher than 200° C., it is difficult to control the reaction and also a side effect proceeds to lower the yield.

When an acrylic acid compound represented by acrylic acid or methacrylic acid is used as the acrylic acid compound, it is desirable to adopt a production method by which water produced as a secondary product during the reaction is removed by azeotropy using an acid catalyst or by using a dehydrant. For removing water by azeotropy, a Dean-Stark water separator or the like can be used. Preferable inorganic acid catalysts include sulfuric acid and the like, and preferable organic acid catalysts include benezenesulfonic acid, p-toluenesulfonic acid and the like. As the dehydrant, any known dehydrant is usable. Preferable dehydrants include concentrated sulfuric acid, boron trifluoride etherate, trifluoroacetic anhydride, dicyclohexylcarbodiimide, 2-halobenzothiazoliumfluoroborate, 2-halogenated pyridinium salt, triphenylphosphine, thionyl chloride/basic compound and the like.

When produced water is removed by azeotropy, a solvent which has low compatibility with water, in which target substance is highly soluble, and which is inactive to the reaction of the present invention is selected. It is preferable to use a solvent exhibiting azeotropy with water in order to remove water produced as a secondary product during the reaction. Examples of such an organic solvent include aliphatic hydrocarbons having a carbon number of 6 to 10 such as hexane, heptane, octane, nonane, decane and the like; alicyclic hydrocarbons having a carbon number of 6 to 10 such as cyclohexane, methylcyclohexane, dimethylcyclohexane, ethylcyclohexane and the like; and aromatic hydrocarbons such as benzene, toluene, xylene, ethylbenzene, cumene, trialkylbenzene and the like. When a dehydrant is used, usable solvents include nitriles such as acetonitrile, benzonitrile and the like; amides such as formamide, acetamide, dimethylformamide, dimethylacetamide and the like; aliphatic hydrocarbons having a carbon number of 6 to 10 such as hexane, heptane, octane, nonane, decane and the like; alicyclic hydrocarbons having a carbon number of 6 to 10 such as cyclohexane, methylcyclohexane, dimethylcyclohexane, ethylcyclohexane and the like; halogenated hydrocarbons; nitro compounds; esters such as ethyl acetate and the like; ethers such as tetrahydrofuran, diethylether, diisopropylether, dioxane and the like; etc. Such solvents may be used independently or in a system of a mixture of two or more. The solvent is used at a ratio of 0.1 to 20 parts by weight, and preferably at 1 to 10 parts by weight, with respect to 1 part by weight of the material. When azeotropy is used, the reaction temperature in the present invention is the azeotropic temperature of the organic solvent to be used and water. The reaction temperature is not limited to this when a dehydrant is used. When the reaction temperature is lower than 60° C., the reaction rate is significantly lowered; and when the reaction temperature is higher than 150° C., the selectivity of the target substance is lowered.

When an acrylic acid ester such as methyl acrylate, methyl methacrylate or the like is used as the acrylic acid compound, the target substance is obtained by removing the corresponding alcohol (methanol in the case of a methoxy group, ethanol in the case of an ethoxy group) to the outside of the reaction system by a known technique such as distillation or the like. Metals and derivatives thereof usable as a catalyst include metals such as tin, titanium, germanium, zinc, lead, cobalt, iron, zirconium, manganese, antimony, potassium and the like, and derivatives thereof. Preferable derivatives include halogen compounds, oxides, carbonates, metal alkoxides, carboxylates and the like. The reaction temperature is 0 to 200° C., and preferably 50 to 150° C. When the reaction temperature is lower than 0° C., the reaction rate is lowered; and when the reaction temperature is higher than 200° C., a side reaction proceeds to lower the yield. For removing the corresponding alcohol to the outside of the reaction system by distillation, the reaction may be carried out near the boiling point of the corresponding alcohol. A solvent in which the material and the target substance are highly soluble and which is inactive to the reaction is desirable. Such solvents include halogen compounds such as dichloromethane, chloroform, 1,2-dichloroethane and the like; ether compounds such as tetrahydrofuran, diethylether, methyl-t-butylether and the like; hydrocarbon compounds such as benzene, toluene, hexane, heptane and the like; and nitrile compounds such as acetonitrile and the like.

The esterification reaction may be carried out after a hydroxyl group of a diol derivative having an alicyclic structure is put into an alcoholate state by an alkali metal such as lithium, sodium or the like; alkyllithium such as butyllithium or the like; or a Grignard reagent such as ethylmagnesium bromide or the like; etc. Namely, the esterification reaction can be carried out after an OH group, which is a hydroxyl group, is converted into an OX group (X is Li, Na, MgBr, MgCl, etc.). As the reaction time of the esterification in the present invention, 0.5 to 100 hours, and preferably 1 to 10 hours, are required. The reaction time depends on the reaction temperature, method of esterification or the like and is determined in accordance with the desired yield or the like, and so is not limited to the above-mentioned range.

In the esterification step, a polymerization inhibitor may be added. Any general polymerization inhibitor is usable with no specific limitation. Usable polymerization inhibitors include nitroso compounds such as 2,2,6,6-tetramethyl-4-hydroxypiperidine-1-oxyl, N-nitrosophenylhydroxylamineammonium salt, N-nitrosophenylhydroxylaminealuminum salt, N-nitroso-N-(1-naphtyl)hydroxylamineammonium salt, N-nitrosodiphenylamine, N-nitroso-N-methylaniline, nitrosonaphthol, p-nitrosophenol, N,N-dimethyl-p-nitrosoaniline and the like; sulfur-containing compounds such as phenothiazine, methylene blue, 2-mercaptobenzoimidazole and the like; amines such as N,N'-diphenyl-p-phenylenediamine, N-phenyl-N-isopropyl-p-phenylenediamine, 4-hydroxydiphenylamine, aminophenol and the like; quinones such as hydroxyquinoline, hydroquinone, methylhydroquinone, p-benzoquinone, hydroquinonemonomethylether and the like; phenols such as methoxyphenol, 2,4-dimethyl-6-t-butylphenol, catechol, 3-s-butylcatechol, 2,2-methylenebis-(6-t-butyl-4-methylphenol) and the like; imides such as N-hydroxyphthalimide and the like; oximes such as cyclohexaneoxime, p-quinonedioxime and the like; dialkylthiodipropinate; and the like. The amount to be added is 0.001 to 10% by weight, and preferably 0.01 to 1% by weight, with respect to the acrylic acid compound.

After the reaction is completed, the reaction solution is washed with water to remove an excessive amount of acrylic acid compound, and an acid or basic additive(s). In this step, the washing water may contain an appropriate inorganic salt such as sodium chloride, sodium hydrogencarbonate or the like. The unreacted acrylic acid compound is removed by washing with alkali. Usable for washing with alkali are an aqueous solution of sodium hydroxide, an aqueous solution of potassium hydroxide, an aqueous solution of sodium carbonate, an aqueous solution of sodium hydrogencarbonate, ammonia water and the like. There is no specific limitation on the alkali component to be used. In order to remove the metal impurities, washing with acid may be performed. Usable for washing with acid are inorganic acids such as an aqueous solution of hydrochloric acid, an aqueous solution of sulfuric acid, an aqueous solution of phosphoric acid; and organic acids such as an aqueous solution of oxalic acid and the like. For performing the washing, an organic solvent may be added to the reaction solution in accordance with the properties of the compound represented by formula (8), which is the material, and of the compound represented by formula (1), which is the product. The organic solvent to be added may be the same as, or different from, the solvent used for the reaction. Usually, it is desirable to use a solvent easily separable from water and having high polarity.

Each of the reaction steps according to the present invention can be performed under normal pressure, under reduced pressure or in a pressurized state. The reaction may be carried out by a commonly used technique such as a batch system, a semi-batch system, a continuous system or the like. In each step, the derivative may be isolated, or may be kept in a dissolved state without being isolated and provided for the next step. After the reaction is completed, the target compound can be easily separated and purified by a common technique, for example, separation means such as filtration, concentration, distillation, extraction, crystallization, recrystallization, column chromatography, purification with activated carbon or the like, or separation means obtained by combining these means.

A polymer according to the present invention is a polymer which contains a repeat unit represented by the following formula (2) and can be produced by single polymerization or copolymerization using an adamantane derivative obtained as described above as a repeat unit.

[Chemical formula 14]

(2)

(in the formula, $R_1$ through $R_3$, which may be the same or different, each represent a hydrogen atom, an alkyl group having a carbon number of 1 to 3, or a halogen-containing alkyl group; $R_4$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or a alkoxy group having a carbon number of 1 to 3; and n represents 14.)

The polymerization reaction is generally carried out as follows. The repeat unit is dissolved in a solvent, and an additive(s) is (are) added. The polymerization reaction is carried out while the components are heated or cooled. The polymerization conditions depend on the type of initiator, initiation method such as heat or light, temperature, pressure, concentration, solvent, additive(s) and the like. As the polymerization to provide the functional resin composition according to the present invention, radical polymerization using a radical generator such as azoisobutylonitrile or the like, ion polymerization using a catalyst such as alkyllithium or the like is generally usable. The method thereof can be a commonly used method.

According to the present invention, the materials of copolymers represented by formula (1) include the following: adamantyl acrylate derivatives such as 2-methyl-2-adamantyl (meth)acrylate, 2-ethyl-2-adamantyl (meth)acrylate, 2-(meth)acryloyloxy-2-(1-adamantyl)propane, 2-(meth)acryloyloxy-2-(1-adamantyl)butane, 3-(meth)acryloyloxy-3-(1-adamantyl)pentane, 3-hydroxy-1-adamantyl (meth)acrylate, 3,5-dihydroxy-1-adamantyl (meth)acrylate and the like; hydroxystyrene derivatives such as hydroxystyrene, α-methylstyrene, 4-t-butoxystyrene, 4-t-butoxycarbonyloxystyrene, 4-t-butoxycarbonylmethyloxystyrene, 4-(2-t-butoxycarbonylethyloxy)styrene and the like; t-butyl (meth)acrylate; isobornyl (meth)acrylate; tricyclodecanyl (meth)acrylate; β-(meth)acryloyloxy γ-butylolactone; β-(meth)acryloyloxy β-methyl-γ-butylolactone; α-(meth)acryloyloxy γ-butylolactone; α-(meth)acryloyloxy α-methyl-γ-butylolactone; α-(meth)acryloyloxy γ,γ-dimethyl-γ-butylolactone; 5-(meth)acryloyloxy 3-oxatricyclo[4.2.1.0$^{4,8}$]nonane-2-one (=9-(meth)acryloyloxy 2-oxatricyclo[4.2.1.0$^{4,8}$]nonane-3-one); 6-(meth)acryloyloxy 3-oxatricyclo[4.3.1.1$^{4,8}$]undecane-2-one; 2-methyl-2-(meth)acryloyloxycyclopentane; 2-ethyl-2-(meth)acryloyloxycyclopentane; and the like. The other repeat units can be present independently or in a mixture of two or more.

The polystyrene-converted weight average molecular weight (hereinafter, referred to as "Mw") of a polymer according to the present invention measured by gel permeation chromatography (GPC) is preferably 1,000 to 150,000, and more preferably 3,000 to 100,000. The ratio of Mw of the polymer with respect to the polystyrene-converted number average molecular weight (hereinafter, referred to as "Mn") of the polymer measured by GPC, i.e., Mw/Mn, is usually 1 to 10, and preferably 1 to 5. According to the present invention, polymers can be used independently or in a mixture of two or more.

A functional resin composition according to the present invention contains a polymer described above and a photoacid generator in a solvent. Resin solvents usually used include, for example, straight-chain ketones such as 2-pentanone, 2-hexanone and the like; cyclic ketones such as cyclopentanone, cyclohexanone and the like; propyleneglycolmonoalkyl acetates such as propyleneglycolmonomethylether acetate, propyleneglycolmonoethylether acetate and the like; ethyleneglycolmonoalkylether acetates such as ethyleneglycolmonomethylether acetate, ethyleneglycolmonoethylether acetate and the like; propyleneglycolmonoalkylethers such as propyleneglycolmonomethylether, propyleneglycolmonoethylether and the like; ethyleneglycolmonoalkylethers such as ethyleneglycolmonomethylether, ethyleneglycolmonoethylether and the like; diethyleneglycolalkylethers such as diethyleneglycoldimethylether, diethyleneglycoldiethylether and the like; esters such as ethyl acetate, ethyl lactate and the like; alcohols such as cyclohexanol, 1-octanol and the like; ethylene carbonate; γ-butylolactone; and the like. These solvents can be used independently or in a mixture of two or more.

A photoacid generator can be appropriately selected from photoacid generators usable as an acid generator for a chemically amplified resist composition, in consideration of the thickness range of the resist coat and the light absorption coefficient of each photoacid generator, in accordance with the wavelength of exposing light. The photoacid generators can be used independently or in a combination of two or more. The amount of the photoacid generator to be used is preferably 0.1 to 20 parts by weight, and more preferably 0.5 to 15 parts by weight, with respect to 100 parts by weight of the resin.

Usable photoacid generators include, for example, onium salt compounds, sulfoneimide compounds, sulfone compounds, sulfonic acid ester compounds, quinonediazide compounds, diazomethane compounds and the like. Among these, onium salt compounds such as sulfonium salt, iodonium salt, phosphonium salt, diazonium salt, pyridinium salt and the like are preferable.

Specific photoacid generators preferably usable for KrF excimer laser light (wavelength 248 nm), ArF excimer laser light (wavelength 193 nm), $F_2$ excimer laser light (wavelength 157 nm), extreme ultraviolet rays (wavelength 13 nm), X rays, electron beams and the like include triphenylsulfoniumtriflate, triphenylsulfoniumhexafluoroantimonate, triphenylsulfoniumnaphthalenesulfonate, (hydroxyphenyl)benzylmethylsulfoniumtoluenesulfonate, diphenyliodoniumtriflate, diphenyliodoniumpyrenesulfonate, diphenyliodoniumdodecylbenzenesulfonate, diphenyliodoniumhexafluoroantimonate, and the like.

An acid diffusion controller having a function of controlling a diffusion phenomenon, in a resist coat, of an acid generated from the acid generator by exposure and of controlling an unfavorable chemical reaction in a non-exposed area can be incorporated. A preferable acid diffusion controller is a nitrogen-containing organic compound, the basicity of which is not changed by exposure or heating which is performed during the step of forming a resist pattern. Such nitrogen-containing organic compounds include, for example, monoalkylamines such as n-hexylamine, n-heptylamine, n-octylamine and the like; dialkylamines such as di-n-butylamine and the like; trialkylamines such as triethylamine and the like; aromatic amines such as aniline, N,N-dimethylaniline, 2-methylaniline, 3-methylaniline, 4-methylaniline, 4-nitroaniline, diphenylamine and the like; amine compounds such as ethylenediamine and the like; amide compounds such formamide, N,N-dimethylformamide, N,N-dimethylacetamide, N-methylpyrrolidone and the like; urea compounds such as urea and the like; imidazoles such as imidazole, benzimidazole and the like; pyridines such as pyridine, 4-methylpyridine and the like; 1,4-diazabicyclo[2.2.2]octane; and the like. The amount of the acid diffusion controller to be incorporated is usually 15 parts by weight or less, preferably 0.001 to 10 parts by weight, and more preferably 0.005 to 5 parts by weight, with respect to 100 parts by weight of the resin.

A functional resin composition according to the present invention can also contain any of various types of additive components which are used in conventional chemically amplified resist compositions, for example, surfactant, quencher, sensitizer, halation inhibitor, preservative/stabilizer, antifoaming agent and other additives when necessary. Preferable sensitizers include, for example, carbazoles, benzophenones, rose bengals, anthracenes and the like.

Usable surfactants include, for example, nonion-based surfactants such as polyoxyethylenelaurylether, polyethyleneglycoldilaurate and the like; and surfactants commercially available under the following trade names: MEGAFAC F170 (produced by DIC Co.); L-70001 (produced by Shin-Etsu Chemical Co., Ltd.); EFTOP EF301, EF303 and EF352 (produced by K.K. Tochem Products); Fluorad FC430 and FC431 (produced by Sumitomo 3M Limited); Asahi Guard AG710, Surflon S-382, SC101, SC102, SC103, SC104, SC105 and SC106 (produced by Asahi Glass Co., Ltd.); KP341 (produced by Shin-Etsu Chemical Co., Ltd.); Polyflow No. 75 and No. 95 (Kyoeisha Chemical Co., Ltd.); and the like.

From a functional resin composition according to the present invention, a resist pattern is formed as follows. The composition solution prepared as described above is applied on a substrate formed of for example, a silicon wafer, a metal, a plastic material, glass, a ceramic material or the like by appropriate application means such as a spin coater, a dip coater, a roller coater or the like. Thus, a resist coat is formed. When necessary, the resist coat is heated at a temperature of about 50° C. to 200° C. in advance, and then is exposed through a prescribed mask pattern. The thickness of the coat is, for example, about 0.01 to 20 μm, and preferably about 0.02 to 1 μm. For the exposure, light rays of any of various wavelengths, for example, ultraviolet rays, X rays or the like are usable. Regarding the light source, for example, any of far-ultraviolet rays from an $F_2$ excimer laser (wavelength 157 nm), an ArF excimer laser (wavelength 193 nm), a KrF excimer laser (wavelength 248 nm) or the like; extreme ultraviolet rays (wavelength: 13 nm); X rays; electron beams and the like is appropriately selected and used. Exposure conditions such as the exposure value are appropriately selected in accordance with the composition particulars of the functional resin composition, the type of additive(s) and the like.

According to the present invention, in order to stably form a high-precision minute pattern, it is preferable to perform heating processing at a temperature of 50° C. to 200° C. for 30 seconds or longer after the exposure. In this step, when the temperature is lower than 50° C., the sensitivity variance depending on the type of the substrate may undesirably spread. After this step, development is performed with an alkaline developer usually under the conditions of 10 to 50° C. for 10 to 200 seconds, and preferably under the conditions of 20 to 25° C. for 15 to 90 seconds. Thus, a prescribed resist pattern is formed.

Usable as an alkaline developer mentioned above is an alkaline aqueous solution obtained by, for example, dissolving an alkaline compound such as an alkali metal hydroxide, ammonia water, an alkylamine, an alkanolamine, a heterocyclic amine, a tetraalkylammoniumhydroxide, corrin, 1,8-diazabicyclo-[5.4.0]-7-undecene, 1,5-diazabicyclo-[4.3.0]-5-nonene or the like, such that the concentration of the alkaline compound is usually 1 to 10% by weight, and preferably 1 to 3% by weight. To the developer formed of the alkaline aqueous solution, a water soluble organic solvent or a surfactant can be incorporated.

EXAMPLES

Hereinafter, the present invention will be described more specifically by way of examples. The present invention is not limited to these examples in any way.

Example 1

In a flask equipped with a stiffer, a thermometer, a dropping funnel, and a Dimroth condenser, 100 g of 1,3-adamantanediol and 1200 g of 96 wt. % concentrated sulfuric acid were put. 50 g of formic acid was dropped thereto over 1 hour, and then these substances were reacted at 25° C. for 10 hours. The reaction solution was added little by little to 2000 g of ice-cooled water. As a result, crystals were deposited. The deposited crystals were suction-filtrated with a glass funnel. As a result, 113 g of 1,3-adamantanedicarboxylic acid was obtained.

In a flask equipped with a stirrer, a thermometer, and a Dimroth condenser, 100 g of 1,3-adamantanedicarboxylic acid, 200 g of methanol, and 20 g of concentrated sulfuric acid were put and heated at 60° C. for 4 hours. After the reaction solution was cooled, 300 mL of ion exchanged water was added thereto. Then, 300 mL of toluene and 300 mL of ethyl acetate were added. The resultant substance was transferred to a separatory funnel to perform liquid/liquid separation. Furthermore, the process of adding 300 mL of toluene and 300 mL of ethyl acetate to the water layer and performing liquid/liquid separation was carried out twice. The toluene/ethyl acetate layer was washed with 200 g of 5 wt. % aqueous solution of sodium hydroxide and 200 mL of ion exchanged water, and then was concentrated. As a result, 91 g of 1,3-adamantanedicarboxylic acid dimethyl was obtained.

In a flask equipped with a stirrer, a thermometer, a dropping funnel, and a Dimroth condenser, 150 g of 1,3-adamantanedicarboxylic dimethyl and 750 mL of tetrahydrofuran were put. 1308 mL of 3 M methylmagnesium chloride/tetrahydrofuran solution was dropped thereto at 10° C. over 4 hours. After the dropping was completed, the resultant substance was stirred at mom temperature for 15 hours. Then, the resultant substance was neutralized with 700 g of 10 wt. % aqueous solution of sulfuric acid while the flask was ice-cooled. The reaction solution was separated into an organic layer and a water layer. The organic layer was washed twice with 500 mL of ion exchanged water, and then was concentrated. The obtained raw product was purified by silica gel column chromatography. As a result, 90 g of 3-(1-hydroxy-1-methylethyl)adamantane-1-carboxylic methylester was obtained.

In a flask equipped with a stirrer, a thermometer, and a rectifying tube, 90 g of 3-(1-hydroxy-1-methylethyl)adamantane-1-carboxylic methyl ester, 43.2 g of potassium-t-butoxide, 450 mL of t-butanol, and 450 mL of toluene were put and heated to 85° C. in an oil bath. The produced methanol was caused to pass through the rectifying tube together with t-butanol and toluene to react these substances for 20 hours while methanol was slowly removed by distillation.

Figure 1:
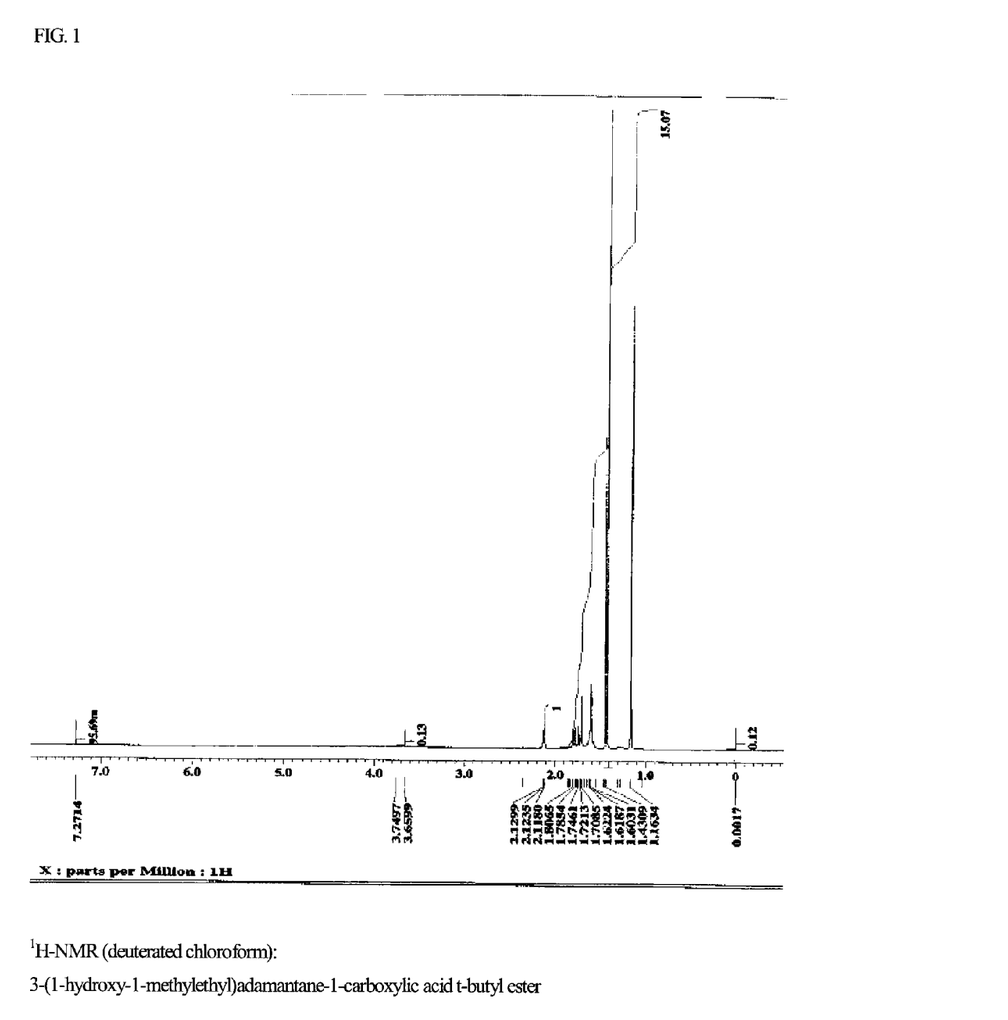
FIG. 1 shows $^1$H-NMR (500 MHz, deuterated chloroform) of white solid 1 in Example 1.

After the reaction, the reaction solution was ice-cooled, and 1000 mL of 10 wt. % aqueous solution of ammonium chloride and 1800 mL of toluene were added thereto. After being stirred, the resultant substance was separated into an organic layer and a water layer. The organic layer was washed twice with 1000 mL of ion exchanged water. The organic layer was concentrated and then purified by silica gel column chromatography. As a result, 57 g of 3-(1-hydroxy-1-methylethyl)adamantane-1-carboxylic acid t-butyl ester was obtained. White solid 1, which was obtained, was identified with $^1$H-NMR (see FIG. 1).

Figure 2:
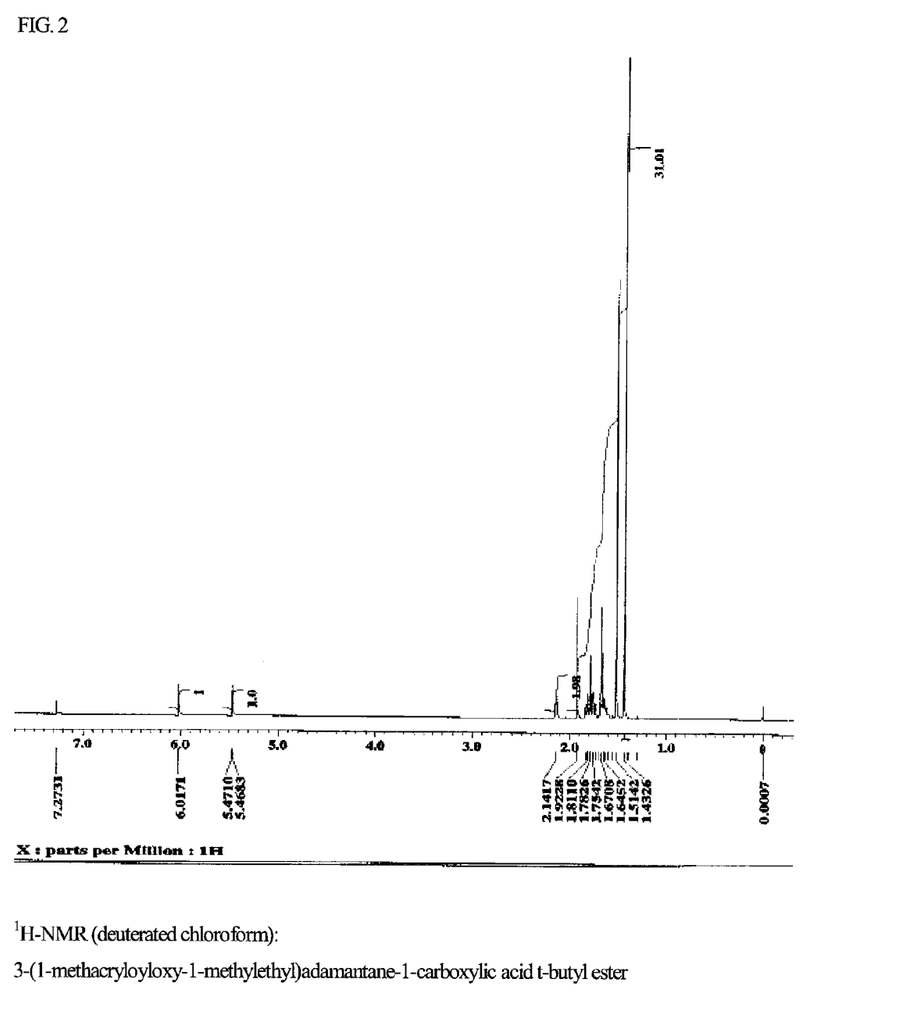
FIG. 2 shows $^1$H-NMR (500 MHz, deuterated chloroform) of white solid 2 in Example 1.
Figure 3:
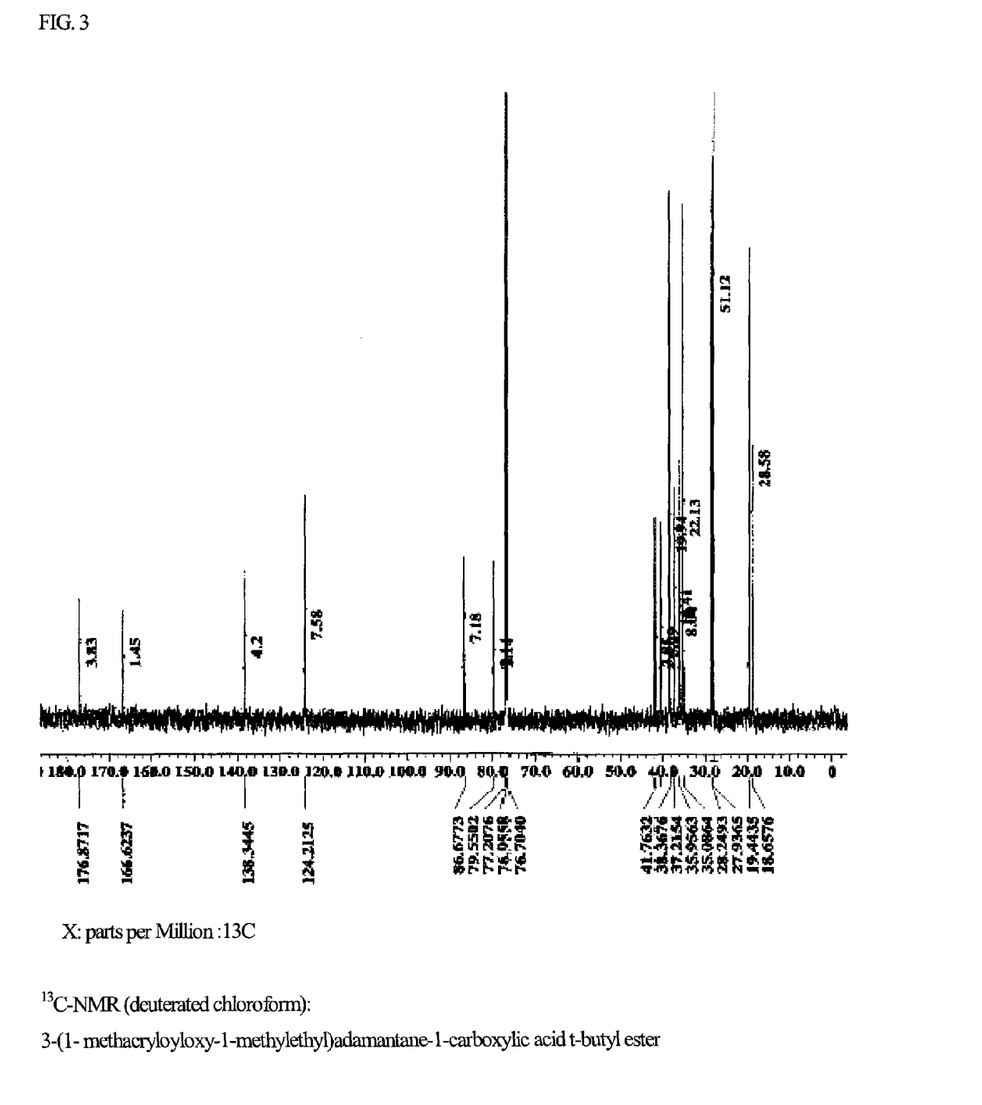
FIG. 3 shows $^{13}$C-NMR (500 MHz, deuterated chloroform) of white solid 2 in Example 1.
Figure 4:
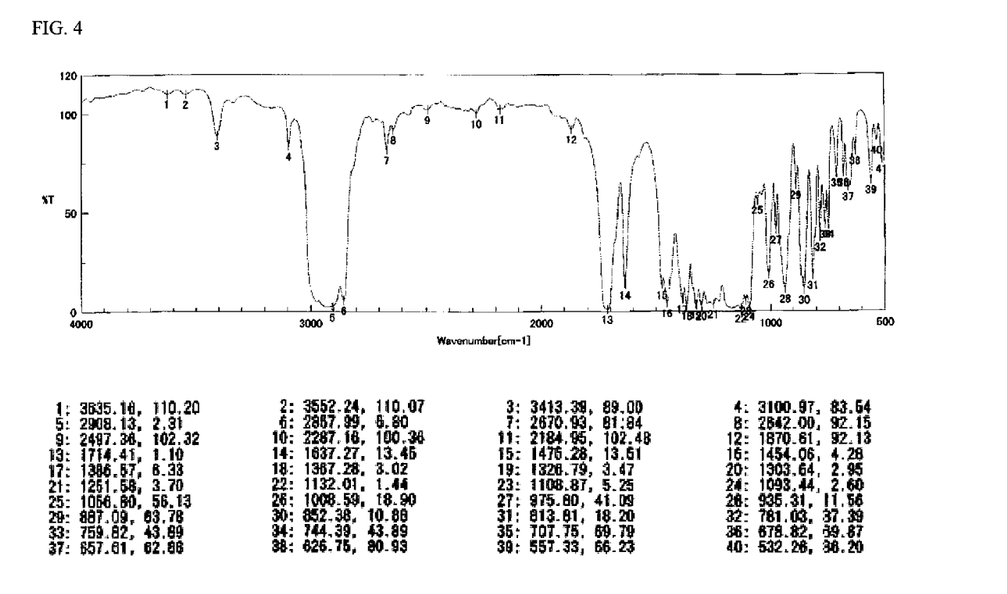
FIG. 4 shows IR of white solid 2 in Example 1.

In a flask equipped with a stirrer, a thermometer, a dropping funnel, and a Dimroth condenser, 50 g of 3-(1-hydroxy-1-methylethyl)adamantane-1-carboxylic acid t-butyl ester, 200 mL of dichloroethane, and 80 g of pyridine were put, and 71.7 g of methacrylic acid chloride was dropped thereto at 60° C. over 2 hours. After the dropping was completed, the resultant substance was stirred at 60° C. for another 8 hours. Then, the resultant substance was neutralized with 320 g of 10% aqueous solution of sulfuric acid while the flask was ice-cooled. The reaction solution was separated into an organic layer and a water layer. The organic layer was washed twice with 500 mL of ion exchanged water, and then was concentrated. The obtained raw product was purified by silica gel column chromatography. As a result, 25 g of 3-(1-methacryloyloxy-1-methylethyl)adamantane-1-carboxylic acid t-butyl ester was obtained as a white solid. White solid 2, which was obtained, was identified with $^1$H-NMR, $^{13}$C-NMR and IR (see FIGS. 2, 3 and 4).

The invention claimed is:

1. An adamantane derivative represented by the following formula (1):

(1)

wherein $R_1$ through $R_3$, which may be the same or different, each represent a hydrogen atom, an alkyl group having a carbon number of 1 to 3, or a halogen-containing alkyl group; $R_4$ and $R_5$ represent methyl, $R_6$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 14.

2. The adamantane derivative according to claim 1, wherein $R_1$ and $R_2$ are each a hydrogen atom; $R_3$ is a hydrogen atom or a methyl group; $R_6$ through $R_8$ are each a methyl group or an ethyl group; and X is a hydrogen atom.

3. A polymer comprising a repeat unit represented by the following formula (2):

(2)

wherein $R_1$ through $R_3$, which may be the same or different, each represent a hydrogen atom, an alkyl group having a carbon number of 1 to 3, or a halogen-containing alkyl group; $R_4$ and $R_5$ represent methyl, $R_6$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 14.

4. A functional resin composition comprising the polymer according to claim 3.

5. The functional resin composition according to claim 4, which is a resin composition for a resist.

6. A method for producing the adamantane derivative represented by formula (1)

(1)

wherein $R_1$ through $R_3$, which may be the same or different, each represent a hydrogen atom, an alkyl group having a carbon number of 1 to 3, or a halogen-containing alkyl group; $R_4$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 14; comprising the steps of:

reacting an adamantane alcohol represented by the following formula (8) and an acrylic acid compound represented by the following formula (9) or (10) to produce the adamantane derivative,

(8)

wherein $R_4$ through $R_8$, which may be the same or different, each represent an alkyl group having a carbon number of 1 to 3 or a halogen-containing alkyl group; X, which may be the same or different, represents a hydrogen atom, an alkyl group having a carbon number of 1 to 3, or an alkoxy group having a carbon number of 1 to 3; and n represents 14, (9)

wherein $R_1$ through $R_3$, which may be the same or different, each represent a hydrogen atom, an alkyl group having a carbon number of 1 to 3, or a halogen-containing alkyl group; and Z represents a hydroxyl group, an alkoxy group, or a halogen group, (10)

wherein $R_1$ through $R_3$, which may be the same or different, each represent a hydrogen atom, an alkyl group having a carbon number of 1 to 3, a halogen-containing alkyl group, or a halogen group.

* * * * *